Figure 1:
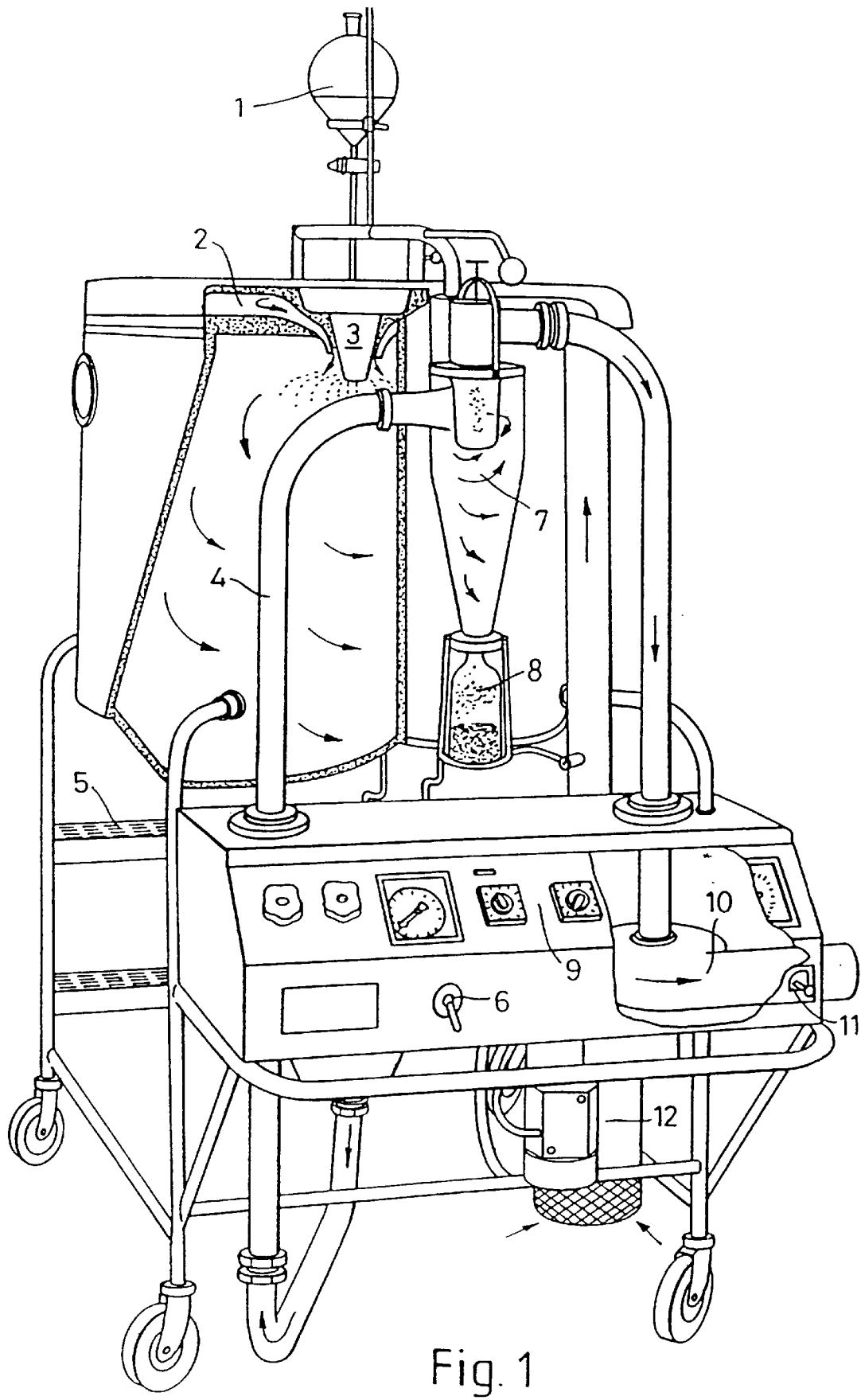

United States Patent

Sutton et al.

[11] Patent Number: 5,957,848
[45] Date of Patent: Sep. 28, 1999

[54] PREPARATION OF FURTHER DIAGNOSTIC AGENTS

[75] Inventors: Andrew Derek Sutton, Ruddington; Richard Alan Johnson, West Bridgford, both of United Kingdom

[73] Assignee: Andaris Limited, Nottingham, United Kingdom

[21] Appl. No.: 08/465,622

[22] Filed: Jun. 5, 1995

Related U.S. Application Data

[63] Continuation of application No. 08/411,815, filed as application No. PCT/GB93/02091, Oct. 8, 1993.

[30] Foreign Application Priority Data

Oct. 10, 1992 [GB] United Kingdom ............. 9221329

[51] Int. Cl.$^6$ ........................................... A61B 8/00
[52] U.S. Cl. .................................... 600/458; 600/431
[58] Field of Search .............. 264/4.3, 4.6; 428/402.2; 424/9, 9.52, 9.5, 9.51; 128/660.01, 660.02, 660.05, 661.04, 662.02; 106/124, 125; 600/431, 433, 458

[56] References Cited

U.S. PATENT DOCUMENTS

| | | | |
|---|---|---|---|
| 2,797,201 | 6/1957 | Veatch et al. | 260/2.5 |
| 3,501,419 | 3/1970 | Bridgeford | 260/2.5 |
| 3,781,230 | 12/1973 | Vassiliades et al. | 260/2.5 |
| 4,089,800 | 5/1978 | Temple | 252/316 |
| 4,102,806 | 7/1978 | Kondo et al. | 252/316 |
| 4,107,288 | 8/1978 | Oppenheim et al. | 424/22 |
| 4,127,622 | 11/1978 | Watanabe et al. | 264/13 |
| 4,173,488 | 11/1979 | Vassiliades et al. | 106/213 |
| 4,276,885 | 7/1981 | Tickner et al. | 128/660 |
| 4,316,391 | 2/1982 | Tickner | 73/861.25 |
| 4,420,442 | 12/1983 | Sands | 264/13 |
| 4,442,843 | 4/1984 | Rasor et al. | 128/660 |
| 4,466,442 | 8/1984 | Hilmann et al. | 128/653 |
| 4,774,958 | 10/1988 | Feinstein | 128/660.01 |

(List continued on next page.)

FOREIGN PATENT DOCUMENTS

| | | |
|---|---|---|
| A-80297/91 | 1/1992 | Australia . |
| 2036107 | 8/1991 | Canada . |
| 0 052 575 | 5/1982 | European Pat. Off. . |
| 0 091 555 | 10/1983 | European Pat. Off. . |
| 0 131 540 | 1/1985 | European Pat. Off. . |

(List continued on next page.)

OTHER PUBLICATIONS

Baveja, S. K. et al., "Microencapsulation of soluble pharmaceuticals," *J. Microencapsulation* 3(1):33–37 (1986).

Beller, G. A. et al., "Assessment of Regional Myocardial Perfusion by Positron Emission Tomography after Intracoronary Administration of Gallium–68 Labeled Albumin Microspheres," *J. Computer Assisted Tomography* 3(4):447–452 (1979).

Cheng, K. T. et al., "The Production and Evaluation of Contrast–Carrying Liposomes Made with an Automatic High–Pressure System," *Investigative Radiol.* 22(1):47–55 (1987).

(List continued on next page.)

*Primary Examiner*—George Manuel
*Attorney, Agent, or Firm*—Sterne, Kessler Goldstein & Fox, P.L.L.C.

[57] ABSTRACT

Microspheres are prepared by a process comprising the steps of (i) spray-drying a solution or dispersion of a wall-forming material in order to obtain intermediate microspheres and (ii) reducing the water-solubility of at least the outside of the intermediate microspheres. Suitable wall-forming materials include proteins such as albumin and gelatin. The microsphere have walls of 40–500 nm thick and are useful in ultrasonic imaging. The control of median size, size distribution and degree of insolubilization and cross-linking of the wall-forming material allows novel microsphere preparations to be produced. In particular, the microspheres may be 15–20 $\mu$m, targeted to selected areas of the body or of prolonged life in the circulation.

4 Claims, 6 Drawing Sheets

U.S. PATENT DOCUMENTS

| | | |
|---|---|---|
| 4,844,882 | 7/1989 | Widder et al. ............................ 424/9 |
| 4,900,540 | 2/1990 | Ryan et al. ............................... 424/9 |
| 4,957,656 | 9/1990 | Cerny et al. ........................... 252/311 |
| 4,960,351 | 10/1990 | Kendall, Jr. et al. ..................... 425/6 |
| 4,968,562 | 11/1990 | Delgado ................................ 428/402 |
| 4,981,625 | 1/1991 | Rhim et al. ............................. 264/13 |
| 5,137,928 | 8/1992 | Erbel et al. ............................ 521/56 |
| 5,147,631 | 9/1992 | Glajch et al. ........................... 424/9 |
| 5,190,982 | 3/1993 | Erbel et al. ............................ 521/56 |
| 5,196,183 | 3/1993 | Yudelson et al. ....................... 424/9 |
| 5,205,287 | 4/1993 | Erbel et al. .......................... 128/632 |
| 5,215,680 | 6/1993 | D'Arrigo ............................... 252/307 |
| 5,271,928 | 12/1993 | Schneider et al. ...................... 424/9 |
| 5,271,961 | 12/1993 | Mathiowitz et al. ............. 427/213.31 |
| 5,380,519 | 1/1995 | Schneider et al. ...................... 424/9 |
| 5,498,421 | 3/1996 | Grinstaff et al. ..................... 424/450 |
| 5,501,863 | 3/1996 | Rössling et al. ..................... 424/489 |
| 5,518,709 | 5/1996 | Sutton et al. ..................... 128/662.02 |
| 5,536,490 | 7/1996 | Klaveness et al. ................. 424/9.52 |
| 5,543,162 | 8/1996 | Timonen et al. ...................... 426/89 |
| 5,547,656 | 8/1996 | Unger ................................... 424/9.4 |
| 5,567,413 | 10/1996 | Klaveness et al. ................. 424/9.51 |
| 5,567,414 | 10/1996 | Schneider et al. ................. 424/9.52 |
| 5,605,673 | 2/1997 | Schutt et al. ......................... 424/9.51 |
| 5,643,553 | 7/1997 | Schneider et al. ................. 424/9.52 |
| 5,658,551 | 8/1997 | Schneider et al. ................. 424/9.51 |

FOREIGN PATENT DOCUMENTS

| | | |
|---|---|---|
| 0 224 934 | 6/1987 | European Pat. Off. . |
| 0 324 938 | 7/1989 | European Pat. Off. . |
| 0 327 490 | 8/1989 | European Pat. Off. . |
| 0 381 543 | 8/1990 | European Pat. Off. . |
| 0 458 079 | 11/1991 | European Pat. Off. . |
| 0 458 745 | 11/1991 | European Pat. Off. . |
| 0 494 615 | 7/1992 | European Pat. Off. . |
| 0 554 213 | 8/1993 | European Pat. Off. . |
| 0 606 486 | 7/1994 | European Pat. Off. . |
| 0 611 567 | 8/1994 | European Pat. Off. . |
| 2 660 864 | 10/1991 | France . |
| 56-129035 | 10/1981 | Japan . |
| 4-145131 | 5/1992 | Japan . |
| 4-506931 | 12/1992 | Japan . |
| 6-507884 | 9/1994 | Japan . |
| 227869 | 11/1992 | New Zealand . |
| 01 89/0873 | 2/1989 | South Africa . |
| 1 288 583 | 9/1972 | United Kingdom . |
| WO 84/02838 | 8/1984 | WIPO . |
| WO 90/13780 | 11/1990 | WIPO . |
| WO 91/06286 | 5/1991 | WIPO . |
| WO 91/09629 | 7/1991 | WIPO . |
| WO 91/12823 | 9/1991 | WIPO . |
| WO 91/15244 | 10/1991 | WIPO . |
| WO 91/16080 | 10/1991 | WIPO . |
| WO 92/05806 | 4/1992 | WIPO . |
| WO 92/17212 | 10/1992 | WIPO . |
| WO 92/17213 | 10/1992 | WIPO . |
| WO 92/18164 | 10/1992 | WIPO . |
| WO 93/02712 | 2/1993 | WIPO . |

OTHER PUBLICATIONS

Clausen, G. et al., "Distribution of blood flow in the dog kidney. III. Local uptake of 10 μ and 15 μm microspheres during renal vasodilation and constriction," *Acta Physiol. Scand.* 113:471–479 (1981).

Cremers, H. F. M. et al., "Albumin–Heparin Microspheres As Carriers for Cytostatic Agents," *J. Controlled Release* 11:167–179 (1990).

Davis, S. S. and L. Illum, "Microspheres As Drug Carriers," in: *Drug Carrier Systems*, F. H. D. Roerdink and A. M. Kroon, eds., New York: John Wiley & Sons, Ltd., pp. 131–153 (1989).

Durand–Keklikian, L. and R. E. Partch, "Microencapsulation of Oil Droplets by Aerosol Techniques—I. Metal Oxide Coatings," *J. Aerosol Sci.* 19(4):511–521 (1988).

Kwok, K. K. et al., "Production of 5–15 μm Diameter Alginate–Polylysine Microcapsules by an Air–Atomization Techniques," *Pharm. Res.* 8(3):341–344 (Mar. 1991).

Levy, M.–C. and M.–C. Andry, "Mixed–walled microcapsules made of cross–linked proteins and polysaccharides: preparation and properties," *J. Microencapsulation* 8(3):335–347 (Sep. 1991).

McArdle, C. S. et al., "Cytotoxic–loaded albumin microspheres: a novel approach to regional chemotherapy," *Br. J. Surg.* 75:132–134 (1988).

Pande, S. et al., "Preparation, characterization and performance evaluation of neomycin–HSA microspheres," *J. Microencapsulation* 7(2):155–165 (1990).

Porter, C. J. H., "The polyoxyethylene/polyoxpropylene block co–polymer Poloxamer–407 selectively redirects intravenously injected microspheres to sinusoidal endothelial cells of rabbit bone marrow," *FEBS Lett.* 305(1):62–66 (Jun. 1992).

Rosenberg, M. et al., "Factors Affecting Retention in Spray–Drying Microencapsulation of Volatile Materials," *J. Agric. Food Chem.* 38:1288–1294 (1990).

Takenaka, H. et al., "Preparation of Enteric–Coated Microcapsules for Tableting by Spray–Drying Technique and In Vitro Simulation of Drug Release from the Tablet in GI Tract," *J. Pharm. Sci.* 69(1):1388–1392 (1980).

Violante, M. R. et al., "Biodistribution of a Particulate Hepatolienographic CT Contrast Agent: A Study of Iodopamide Ethyl Ester in the Rat," *Investigative Radiol.* 16(1):40–45 (1981).

White, C. et al., "Biodistribution and Clearance of Contrast–Carrying MREV Liposomes," *Investigative Radiol.* 25(10):1125–1129 (1990).

Wilkins, D. J. and P. A. Myers, "Studies on the Relationship Between the Electrophoretic Properties of Colloids and Their Blood Clearance and Organ Distribution in the Rat," pp. 568–576.

Zhang, D. et al., "Histochemical studies on the mechanism of macromolecule leakage across the glomerular capillary wall," *Histochem.* 96:115–121 (Jun. 1991).

Cremers, H. F. M. et al., "Albumin–Heparin Microspheres As Carriers for Cytostatic Agents," *J. Controlled Release* 11:167–179 (1990).

English Language Translation of Japanese Patent No. 56–129035 (Document AM6).

English Language Abstract of Japanese Patent No. 56–129035 (Document AM6), Patent Abstracts of Japan (JPO and Japio, 1981).

English Language Abstract of Japanese Patent No. 04–145131 (Document AN6), Patent Abstracts of Japan (JPO and Japio, 1992).

Aldrich, J.E. and Johnston, J.R., "Use of the Spinning Disk Technique to Produce Monodisperse Microspheres of Human Serum Albumin for Labelling with Radioisotopes," *Int. J. Appl. Radiat. Isotopes* 25:15–18 (1974).

Barnhart, J., et al., "Characteristics of Albunex: Air–Filled Albumin Microspheres for Echocardiography Contrast Enhancement," *Invest. Radiol.* 25:S162–S164 (1990).

Basu, S. and Bhattacharya, G., "Some Aspects of the Phenomenon of Coacervation," *Science* 115:544–545 (1952).

Conte, U., et al., "Spray Dried Albumin Microspheres Containing Nicardipine," *Eur. J. Pharm. Biopharm.* 40(4):203–208 (Aug. 1994).

Ellison, J. McK., "Adaptation of the Spinning Top Generator to Provide Aerosols in the Respirable Range," *Ann. Occup. Hyg.* 10:363–367 (1967).

Feinstein, S.B. et al., "Microbubble Dynamics Visualized in the Intact Capillary Circulation," *J. Am. Coll. Cardiol.* 4(3):595–600 (1984).

Galyean, R.D. and Cotterill, O.J., "Chromatography and Electrophoresis of Native and Spray–Dried Egg White," *J. Food Sci.* 44:1345–1349 (1979).

Grinstaff, M.W. and Suslick, K.S., "Air–filled proteinaceous microbubbles: Synthesis of an echo–contrast agent," *Proc. Natl. Acad. Sci. USA* 88:7708–7710 (Sep. 1991).

Gupta, P.K. and Hung, C.T., "Albumin microspheres I: physico–chemical characteristics," *J. Microencapsulation* 6(4):427–462 (1989).

Haghpanah, M., et al., abstract presented at British Pharmaceutical Conference, King's College, London (1991).

Heller, J., "Controlled release of biologically active compounds from bioerodible polymers," *Biomaterials* 1:51–57 (1980).

Kawashima, Y. et al., "Preparation of multiple unit hollow microspheres (microballoons) with acrylic resin containing tranilast and their drug release characteristics (in vitro) and floating behavior (in vivo)," *J. Contr. Rel.* 16(3):279–290 (Aug. 1991).

Kondo, A., "Microcapsule Processing and Technology," Van Valkenburg, J.W. (Ed.), New York: Marcel Dekker, Inc., pp. 18–20, 61, 68, 70, 90–92, 106–109, 118–119 (1980).

Modler, H.W. and Emmons, D.B., "Calcium as an Adjuvant for Spray–Drying Acid Whey," *J. Dairy Sci.* 61(3):294–299 (1978).

Ophir, J. et al., "Aqueous Solutions as Potential Ultrasonic Contrast Agents," *Ultrasonic Imaging* 1(3):265–279 (1979).

Ophir, J. et al., "Ultrasonic Backscatter from Contrast Producing Collagen Microspheres," *Ultrasonic Imaging* 2:67–77 (1980).

Parkinson, T.L., "Effects of Spray–Drying and Freezing on the Proteins of Liquid Whole Egg," *J. Sci. Fd Agric.* 26:1625–1637 (1975).

Raju, A. et al., "Human Serum Albumin Microspheres for Lung Imaging—Preparation and Evaluation," *Isotopenpraxis* 14(2):57–61 (1978).

Sato, T. et al., "Porous Biodegradable Microspheres for Controlled Drug Delivery. I. Assessment of Processing Conditions and Solvent Removal Techniques," *Pharm. Res.* 5(1):21–30 (1988).

Scheffel, U. et al., "Albumin Microspheres for Study of the Reticuloendothelial System," *J. Nucl. Med.* 13(7):498–503 (1972).

Schlief, R., "Ultrasound contrast agents," *Curr. Opin. Radiol.* 3:198–207 (1991).

Schneider, M. et al., "Polymeric Microballoons as Ultrasound Contrast Agents—Physical and Ultrasonic Properties Compared with Sonicated Albumin," *Investig. Radiol.* 27(2):134–139 (Feb. 1992).

Shapiro, J.R. et al., "Intravenous Contrast Echocardiography With Use of Sonicated Albumin in Humans: Systolic Disappearance of Left Ventricular Contrast After Transpulmonary Transmission," *J. Am. Coll. Cardiol.* 16(7):1603–1607 (1990).

Takenaka, H. et al., "Mechanical Properties, Dissolution Behavior and Stability to Oxidation of L–Ascorbyl-monostearate Microcapsules prepared by a Spray–Drying Polycondensation Technique," *Chem. Pharm. Bull.* 30(6):2189–2195 (1982).

Wheatley, M.A. et al., "Contrast agents for diagnostic ultrasound: development and evaluation of polymer–coated microbubbles," *Biomaterials* 11:713–717 (1990).

Widder, K.J. et al., "Magnetically Responsive Microspheres and Other Carriers for the Biophysical Targeting of Antitumor Agents," *Adv. Pharmacol. Chemother.* 16:213–271 (1979).

PREPARATION OF FURTHER DIAGNOSTIC AGENTS

CROSS-REFERENCE TO RELATED APPLICATION

This application is a continuation of prior U.S. patent application No. 08/411,815, filed Apr. 10, 1995 (pending), which is a 371 of PCT/GB93/0209, filed Oct. 8, 1993.

The present invention relates to the preparation of diagnostic agents comprising hollow microcapsules used to enhance ultrasound imaging.

The fact that air bubbles in the body can be used for echocardiography has been known for some time. Bubble-containing liquids can be injected into the bloodstream for this purpose (see Ophir et al (1980) "*Ultrasonic Imaging*" 2, 67–77, who stabilised bubbles in a collagen membrane, U.S. Pat. No. 4,446,442 (Schering) and EP-A-131 540 (Schering)) and U.S. Pat. No. 4,718,433, U.S. Pat. No. 4,774,958 and U.S. Pat. No. 4,844,882 disclose the use of bubbles prepared by sonicating an albumin solution. However, the size distribution of the bubbles is apparently uncontrollable and the bubbles disappear when subjected to pressure experienced in the left ventricle (Shapiro et al (1990) *J. Am. Coll. Cardiology*, 16(7), 1603–1607).

EP-A-52575 discloses, for the same purpose, solid particles which have gas entrained in them, the gas being released from the particles in the bloodstream.

EP 458 745 (Sintetica) discloses a process of preparing air- or gas-filled microballoons by interfacial polymerisation of synthetic polymers such as polylactides and polyglycolides. WO 91/12823 (Delta Biotechnology) discloses a similar process using albumin. Wheatley et al (1990) *Biomaterials* 11, 713–717 discloses ionotropic gelation of alginate to form microbubbles of over 30 $\mu$m diameter. WO 91/09629 discloses liposomes for use as ultrasound contrast agents. Our co-pending patent application PCT/GB92/00643 (published since the priority date of this application as WO 92/18164) discloses a spray-drying method which leads to particularly advantageous microspheres having the required strength and tightly controlled size distribution. Other spray-drying processes, for different purposes, were disclosed in Przyborowski et al (1982 *Eur. J. Nucl. Med.* 7, 71–72), namely the preparation of human serum albumin (HSA) microspheres for radiolabelling and subsequent use in scintigraphic imaging of the lung.

The Przyborowski et al article refers to two earlier disclosures of methods of obtaining albumin particles for lung scintigraphy. Aldrich & Johnston (1974) *Int. J. Appl. Rad. Isot.* 25, 15–18 disclosed the use of a spinning disc to generate 3–70 $\mu$m diameter particles which are then denatured in hot oil. The oil is removed and the particles labelled with radioisotopes. Raju et al (1978) *Isotopenpraxis* 14(2), 57–61 used the same spinning disc technique but denatured the albumin by simply heating the particles. In neither case were hollow microspheres mentioned and the particles prepared were not suitable for echocardiography.

We have now developed our previous spray-drying process (WO 92/18164) and adapted it to produce further advantageous products.

One aspect of the present invention provides a process comprising a first step of atomising a solution or dispersion of a wall-forming material in order to obtain (i) hollow microspheres of 15–20 $\mu$m diameter, (ii) hollow microspheres having a prolonged half-life in the human bloodstream or (iii) hollow microspheres which are adapted for selective targeting to an area of the human or animal body.

These three microsphere products will be termed herein "the large microspheres", "the long life microspheres" and "the targeted microspheres", respectively.

Preferably, the product obtained in the said process is subjected to a second step of reducing the water-solubility of at least the outside of the said microspheres.

The said two steps may be carried out as a single process or the intermediate product of the first step may be collected and separately treated in the second step. These two possibilities are referred to hereinafter as the one step and two step processes.

The wall-forming material and process conditions should be so chosen that the product is sufficiently non-toxic and non-immunogenic in the conditions of use, which will clearly depend on the dose administered and duration of treatment. The wall-forming material may be a starch derivative, a synthetic polymer such as tert-butyloxycarbonylmethyl polyglutamate (U.S. Pat. No. 4,888,398) or a polysaccharide such as polydextrose or starch.

Generally, the wall-forming material can be selected from most hydrophilic, biodegradable physiologically compatible polymers. Among such polymers one can cite polysaccharides of low water solubility, polylactides and polyglycolides and their copolymers, copolymers of lactides and lactones such as $\epsilon$-caprolactone, $\delta$-valerolactone, polypeptides, and proteins such as gelatin, collagen, globulins and albumins. Other suitable polymers include poly (ortho)esters (see for instance U.S. Pat. No. 4,093,709; U.S. Pat. No. 4,131,648; U.S. Pat. No. 4,138,344; U.S. Pat. No. 4,180,646; polylactic and polyglycolic acid and their copolymers, for instance DEXON (see J. Heller (1980) *Biomaterials* 1, 51; poly(DL-lactide-co-$\delta$-caprolactone), poly(DL-lactide-co-$\delta$-valerolactone), poly(DL-lactide-co-g-butyrolactone), polyalkylcyanoacrylates; polyamides, polyhydroxybutyrate; polydioxanone; poly-$\beta$-aminoketones (*Polymer*23 (1982), 1693); polyphosphazenes (*Science* 193 (1976), 1214); and polyanhydrides. References on biodegradable polymers can be found in R. Langer el al (1983) *Macromol. Chem. Phys.* C23, 61–125. Polyamino-acids such as polyglutamic and polyaspartic acids can also be used as well as their derivatives, ie partial esters with lower alcohols or glycols. One useful example of such polymers is poly-(t,butyl-glutamate). Copolymers with other amino-acids such as methionine, leucine, valine, proline, glycine, alamine, etc are also possible. Recently some novel derivatives of polyglutamic and polyaspartic acid with controlled biodegradability have been reported (see WO 87/03891; U.S. Pat. No. 4,888,398 and EP 130 935 incorporated here by reference). These polymers (and copolymers with other amino-acids) have formulae of the following type:

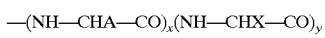

where X designates the side chain of an amino-acid residue and A is a group of formula —$(CH_2)_n COOR^1 R^2 OCOR$(II), with $R^1$ and $R^2$ being H or lower alkyls, and R being alkyl or aryl; or R and $R^1$ are connected together by a substituted or unsubstituted linking member to provide 5- or 6-membered rings.

A can also represent groups of formulae:

and

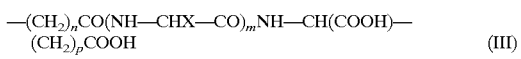

and corresponding anhydrides. In all these formulae n, m and p are lower integers (not exceeding 5) and x and y are also integers selected for having molecular weights not below 5000.

The aforementioned polymers are suitable for making the microspheres according to the invention and, depending on the nature of substituents R, $R^1$, $R^2$ and X, the properties of the wall can be controlled, for instance, strength, elasticity and biodegradability. For instance X can be methyl (alanine), isopropyl (valine), isobutyl (leucine and isoleucine) or benzyl (phenylalanine).

Preferably, the wall-forming material is proteinaceous. For example, it may be collagen, gelatin or (serum) albumin, in each case preferably of human origin (ie derived from humans or corresponding in structure to the human protein). Most preferably, it is human serum albumin (HA) derived from blood donations or from the fermentation of microorganisms (including cell lines) which have been transformed or transfected to express HA.

Techniques for expressing HA (which term includes analogues and fragments of human albumin, for example those of EP-A-322094, and polymers of monomeric albumin) are disclosed in, for example, EP-A-201239 and EP-A-286424. All references are included herein by reference. "Analogues and fragments" of HA include all polypeptides (i) which are capable of forming a microsphere in the process of the invention and (ii) of which a continuous region of at least 50% (preferably at least 75%, 80%, 90% or 95%) of the amino acid sequence has at least 80% sequence identity (preferably at least 90%, 95% or 99% identity) with a continuous region of at least 50% (preferably 75%, 80%, 90% or 95%) of human albumin. HA which is produced by recombinant DNA techniques is particularly preferred. Thus, the HA may be produced by expressing an HA-encoding nucleotide sequence in yeast or in another microorganism and purifying the product, as is known in the art.

In the following description of preferred embodiments, the term "protein" is used since this is what we prefer but it is to be understood that other biocompatible wall-forming materials can be used, as discussed above.

The protein solution or dispersion is preferably 0.1 to 50% w/v, more preferably about 5.0–25.0% protein, particularly when The protein is albumin. About 20% is optimal. Mixtures of wall-forming materials may be used, in which case the percentages in the last two sentences refer lo the total content of wall-forming material.

The preparation to be sprayed may contain substances other than the wall-forming material and solvent or carrier liquid. Thus, the aqueous phase may contain 1–20% by weight of water-soluble hydrophilic compounds like sugars and polymers as stabilizers, eg polyvinyl alcohol (PVA), polyvinyl pyrrolidone (PVP), polyethylene glycol (PEG), gelatin, polyglutamic acid and polysaccharides such as starch, dextran, agar, xanthan and the like. Similar aqueous phases can be used as the carrier liquid in which the final microsphere product is suspended before use. Emulsifiers may be used (0.1–5% by weight) including most physiologically acceptable emulsifiers, for instance egg lecithin or soya bean lecithin, or synthetic lecithins such as saturated synthetic lecithins, for example, dimyristoyl phosphatidyl choline, dipalmitoyl phosphatidyl choline or distearoyl phosphatidyl choline or unsaturated synthetic lecithins, such as dioleyl phosphatidyl choline or dilinoleyl phosphatidyl choline. Emulsifiers also include surfactants such as free fatty acids, esters of fatty acids with polyoxyalkylene compounds like polyoxypropylene glycol and polyoxyethylene glycol; ethers of fatty alcohols with polyoxyalkylene glycols; esters of fatty acids with polyoxyalkylated sorbitan; soaps; glycerol-polyalkylene stearate; glycerol-polyoxyethylene ricinoleate; homo- and copolymers of polyalkylene glycols; polyethoxylated soya-oil and castor oil as well as hydrogenated derivatives; ethers and esters of sucrose or other carbohydrates with fatty acids, fatty alcohols, these being optionally polyoxyalkylated; mono-, di- and triglycerides of saturated or unsaturated fatty acids, glycerides or soya-oil and sucrose.

Additives can be incorporated into the wall of the microspheres to modify the physical properties such as dispersibility, elasticity and water permeability.

Among the useful additives, one may cite compounds which can "hydrophobize" the wall in order to decrease water permeability, such as fats, waxes and high molecular-weight hydrocarbons. Additives which improve dispersibility of the microspheres in the injectable liquid-carrier are amphipathic compounds like the phospholipids, they also increase water permeability and rate of biodegradability.

Additives which increase wall elasticity are the plasticizers like isopropyl myristate and the like. Also, very useful additives are constituted by polymers akin to that of the wall itself but with relatively low molecular weight. For instance when using copolymers of polylactic/polyglycolic type as the wall-forming material, the properties of the wall can be modified advantageously (enhanced softness and biodegradability) by incorporating, as additives, low molecular weight (1000 to 15,000 Dalton) polyglycolides or polylactides. Also polyethylene glycol of moderate to low MW (eg PEG 2000) is a useful softening additive.

The quantity of additives to be incorporated in the wall is extremely variable and depends on the needs. In some cases no additive is used at all; in other cases amounts of additives which may reach about 20% by weight of the wall are possible.

The protein solution or dispersion (preferably solution), referred to hereinafter as the "protein preparation", is atomised and spray-dried by any suitable technique which results in discrete microspheres of 1.00–50.0 μm diameter. These figures refer to at least 90% of the population of microspheres, the diameter being measured with a Coulter Master Sizer II. The term "microspheres" means hollow particles enclosing a space, which space is filled with a gas or vapour, but not with any solid materials. Honeycombed particles resembling the confectionery sold in the UK as "Maltesers" (Regd TM) are not formed. It is not necessary for the space lo be totally enclosed (although this is preferred) and it is not necessary for the microspheres to be precisely spherical, although they are generally spherical. If the microspheres are not spherical, then the diameters referred to above relate to the diameter of a corresponding spherical microsphere having the same mass and enclosing the same volume of hollow space as the non-spherical microsphere.

The atomising comprises forming an aerosol of the protein preparation by, for example, forcing the preparation through at least one orifice under pressure into, or by using a centrifugal atomizer in, a chamber of warm air or other inert gas. The chamber should ideally be big enough for the largest ejected drops not to strike the walls before drying. The gas or vapour in the chamber is clean (ie preferably sterile and pyrogen-free) and non-toxic when administered into the bloodstream in the amounts concomitant with administration of the microspheres in echocardiography. The rate of evaporation of the liquid from the protein preparation should be sufficiently high to form hollow microspheres but not so high as to burst the microspheres. The rate of evaporation may be controlled by varying the gas flow rate, concentration of protein in the protein preparation, nature of liquid carrier, feed rate of the solution and, most importantly, the temperature of the gas encountered by the aerosol. With an albumin concentration of 15–25% in water, an inlet gas temperature of at least about 100° C., preferably at least 110° C., is generally sufficient lo ensure hollowness and the temperature may be as high as 250° C. without the capsules bursting. About 180–240° C., preferably about 210–230° C. and most preferably about 220° C., is optimal, at least for albumin. The temperature may, in the one step version of the process of the invention, be sufficient to insolubilise at least part (usually the outside) of the wall-forming material and frequently substantially all of the wall-forming material. Since the temperature of the gas encountered by the aerosol will depend also on the rate at which the aerosol is delivered and on the liquid content of the protein preparation, the outlet temperature may be monitored to ensure an adequate temperature in the chamber. An outlet temperature of 40–150° C. has been found to be suitable. Apart from this factor, however, controlling the flow rate has not been found to be as useful as controlling the other parameters.

In the two step process, the intermediate microspheres comprise typically 96–98% monomeric HA and have a limited in vivo life time for ultrasound imaging. They may, however, be used for ultrasound imaging (at least in some uses of the microspheres of the invention), or they may be stored and transported before the second step of the two step process is carried out. They therefore form a further aspect of the invention.

In the second step of the process, the intermediate microspheres prepared in the first step are fixed and rendered less water-soluble so that they persist for longer whilst not being so insoluble and inert that they are not biodegradable. This step also strengthens the microspheres so that they are better able to withstand the rigours of administration, vascular shear and ventricular pressure. If the microspheres burst, they become less echogenic. Schneider et al (1992) *Invest. Radiol.* 27, 134–139 showed that prior art sonicated albumin microbubbles do not have this strength and rapidly lose their echogenicity when subjected to pressures typical of the left ventricle. The second step of the process may employ heat (for example microwave heat, radiant heat or hot air, for example in a conventional oven), ionising irradiation (with, for example, a 10.0–100.0 kGy dose of gamma rays) or chemical cross-linking using, for example, formaldehyde, glutaraldehyde, ethylene oxide or other agents for cross-linking proteins and is preferably carried out on the substantially dry intermediate microspheres formed in the first step, or on a suspension of such microspheres in a liquid in which the microspheres are insoluble, for example a suitable solvent. In the one step version of the process, a cross-linking agent such as glutaraldehyde may be sprayed into the spray-drying chamber or may be introduced into the protein preparation just upstream of the spraying means. Alternatively, the temperature in the chamber may be high enough to insolubilise the microspheres.

The "long life microspheres" and the "targeted microspheres" may, if one wishes, consist of microspheres having a diameter of 0.05 to 50.0 $\mu$m (measured in the same way as the intermediate microspheres), but ranges of 0.1 to 20.0 $\mu$m and especially 1.0 to 8.0 $\mu$m are obtainable with the process of the invention and are preferred for echocardiography. We have found that a range of about 0.5 to 3.0 $\mu$m may be especially suitable for the production of a low contrast image and for use in colour Doppler imaging, whereas a range of about 4.0 to 6.0 $\mu$m may be better for the production of sharp images. One needs to take into account the fact that the second step may alter the size of the microspheres in determining the size produced in the first step.

It has been found that the process of the invention can be controlled in order to obtain microspheres with desired characteristics. Thus, the pressure at which the protein solution is supplied to the spray nozzle may be varied, for example from 1.0–10.0×10$^5$ Pa, preferably 2.0–6.0×10$^5$ Pa and most preferably about 5×10$^5$ Pa. Other parameters may be varied as disclosed above and below. In this way, novel microspheres may be obtained.

A further aspect of the invention provides large, long life or targeted hollow microspheres in which more than 30%, preferably more than 40%, 50%, or 60%, of the microspheres have a diameter within a 2 $\mu$m range and, in the case of the long life or targeted microspheres, at least 90%, preferably at least 95% or 99%, have a diameter within the range 1.0–8.0 $\mu$m. In the case of the large microspheres, the corresponding diameter range is 12–25 $\mu$m.

Thus, the interquartile range may be 2 $\mu$m, with a median diameter (for the long life or targeted microspheres) of 3.5, 4.0, 4.5, 5.0, 5.5, 6.0 or 6.5 $\mu$m.

Thus, at least 30%, 40%, 50% or 60% of the long life or targeted microspheres may have diameters within the range 1.5–3.5 $\mu$m, 2.0–4.0 $\mu$m, 3.0–5.0 $\mu$m, 4.0–6.0 $\mu$m, 5.0–7.0 $\mu$m or 6.0–8.0 $\mu$m. Preferably a said percentage of the said microspheres have diameters within a 1.0 $\mu$m range, such as 1.5–2.5 $\mu$m, 2.0–3.0 $\mu$m, 3.0–4.0 $\mu$m, 4.0–5.0 $\mu$m, 5.0–6.0 $\mu$m, 6.0–7.0 $\mu$m or 7.0–8.0 $\mu$m.

A further aspect of the invention provides large, long life or targeted hollow microspheres with proteinaceous walls in which at least 90%, preferably at least 95% or 99%, of the microspheres have a diameter in the range 1.0–8.0 $\mu$m (or, in the case of the large microspheres, 12–25 $\mu$m); at least 90%, preferably at least 95% or 99%, of the microspheres have a wall thickness of 40–500 nm, preferably 100–500 nm; and at least 50% of the protein in the walls of the microspheres is cross-linked.

Scanning electron microscopy of the microcapsules shows that they are hollow spheres with no solid matter other than in the wall. Hence, the wall thickness can either be measured microscopically or can be calculated as follows. The mass of wall-forming material in each of the sprayed droplets is given by $$\text{Mass} = (\text{volume of droplet}) \times \quad \text{(I)}$$
$$(\text{concentration of wall-forming material in solution sprayed})$$
$$= \frac{4}{3}\pi r_e^3 c$$

where $r_e$ is the radius of the droplet and c is the said concentration.

Our studies have shown that the external dimension of the droplet is essentially unchanged whilst the solvent is evaporated off. The mass of wall-forming material in the dried microcapsule is therefore given by $$\text{mass} = \frac{4}{3}\pi(r_e^3 - r_i^3)\rho \quad \text{(II)}$$

where $r_e$ is the external radius of the microcapsule (same as that of the droplet), $r_i$ is the internal radius of the microcapsule and p is the density of the wall-forming material. The wall thickness is then represented by $r_e$–$r_i$. The quantity $r_e$ is known from straightforward measurement of the microcapsules using a Coulter Counter, and $r_i$ is obtained by $$r_i = \sqrt[3]{r_e^3 - \frac{r_e^3 c}{\rho}} \quad \text{(III)}$$

Hence, for an external diameter of 5 μm (external radius of 2.5 μm), a concentration in the solution sprayed of 0.2 g/ml (20%) and a wall density of 1.31 g/cm³ (determinable by helium pycnometry). the wall thickness can be calculated to be 134 nm.

Preferably, at least 75%, 90%, 95%, 98.0%, 98.5% or 99% of the protein in any of the three kinds of microspheres of the invention is sufficiently cross-linked to be resistant to extraction with a 1% HCl solution for 2 minutes. Extracted protein is detected using the Coomassie Blue protein assay, Bradford. The protein content in the washings is expressed as a percentage of the original mass of microcapsules.

The degree of cross-linking is controlled by varying the heating, irradiation or chemical treatment of the protein. During the cross-linking process, protein monomer is cross-linked and quickly becomes unavailable in a simple dissolution process, as detected by gel permeation HPLC or gel electrophoresis, as is shown in Example 8 below. Continued treatment leads to further cross-linking of already cross-linked material such that it becomes unavailable in the HCl extraction described above. During heating at 175° C., rHA microspheres in accordance with the invention lose about 99% of HCl-extractable protein over the course of 20 minutes, whereas, at 150° C., 20 minutes' heating removes only about 5% HCl-extractable protein, 30 mins removes 47.5%, 40 mins 83%, 60 mins 93%, 80 mins 97% and 100 mins removes 97.8% of the HCl-extractable protein. To achieve good levels of cross-linking therefore, the microspheres may be heated at 175° C. for at least 17 (preferably 20–40 mins, most preferably 35–40 mins) mins, at 150° C. for at least 80 mins and at other temperatures for correspondingly longer or shorter times. We have found that serum-derived albumin needs less time to cross-link than rHA.

The injectable microspheres of the present invention can be stored dry in the presence or in the absence of additives to improve conservation and prevent coalescence. As additives, one may select from 0.1 to 25% by weight of water-soluble physiologically acceptable compounds such as mannitol, galactose, lactose or sucrose or hydrophilic polymers like dextran, xanthan, agar, starch, PVP, polyglutamic acid, polyvinylalcohol (PVA) and gelatin.

In order to minimise any agglomeration of the microspheres, the microspheres can be milled with a suitable inert excipient using a Fritsch centrifugal pin mill equipped with a 0.5 mm screen, or a Glen Creston air impact jet mill. Suitable excipients are finely milled powders which are inert and suitable for intravenous use, such as lactose, glucose, mannitol, sorbitol, galactose, maltose or sodium chloride. Once milled, the microspheres/excipient mixture can be suspended in aqueous medium to facilitate removal of non-functional/defective microspheres. Upon reconstitution in the aqueous phase, it is desirable to include a trace amount of surfactant to prevent agglomeration. Anionic, cationic and non-ionic surfactants suitable for this purpose include poloxamers, sorbitan esters, polysorbates and lecithin.

The microsphere suspension may then be allowed to float, or may be centrifuged to sediment any defective particles which have surface defects which would, in use, cause them to fill with liquid and be no longer echogenic.

The microsphere suspension may then be remixed to ensure even particle distribution, washed and reconstituted in a buffer suitable for intravenous injection such as 0.15M NaCl 0.01 mM Tris pH 7.0. The suspension may be aliquoted for freeze drying and subsequent sterilisation by, for example, gamma irradiation, dry heating or ethylene oxide.

An alternative method for deagglomeration of the insolubilised or fixed microspheres is to suspend them directly in an aqueous medium containing a surfactant chosen from poloxamers, sorbitan esters, polysorbates and lecithin. Deagglomeration may then be achieved using a suitable homogeniser.

The microsphere suspension may then be allowed to float or may be centrifuged to sediment the defective particles, as above, and further treated as above.

Although the microspheres of this invention can be marketed in The dry state, more particularly when they are designed with a limited life time after injection, it may be desirable to also sell ready-made preparations, ie suspensions of microspheres in an aqueous liquid carrier ready for injection.

The product is generally, however, supplied and stored as a dry powder and is suspended in a suitable sterile, non-pyrogenic liquid just before administration.

A further aspect of the invention provides large, long life or targeted hollow microspheres, at least 10% of the microspheres, when suspended in water, being capable of surviving a 0.25 s application of a pressure of 2.66×10$^4$ Pa without bursting, collapsing or filling with water: The transient maximum pressure in the human left ventricle is about 200 mmHg (2.66×10$^4$ Pa). Preferably 50%, 75%, 90% or 100% survive the said 0.25 s application of 2.66×10$^4$ Pa when tested as above, ie remain echogenic. In vivo, preferably the same percentages will remain echogenic during one passage through both ventricles of the heart.

The "large" microspheres of the invention are characterised by the fact that at least 90%, preferably at least 95% or 99%, of the microspheres have a diameter within the range 10.1–19.9 μm, preferably 13–18 μm.

It should be noted that these microspheres are "large" only in relation to the preferred microspheres of our earlier patent application WO 92/18164 and in relation to the preferred sizes of long life and targeted microspheres disclosed herein; prior art microspheres were frequently larger than 25 μm.

The large microspheres of the invention may be produced by controlling the parameters of the spray-drying process. The concentration of The wall-forming material in the liquid lo be sprayed may be the same as for the smaller microspheres described above, namely 0.1–50.0% w/v (preferably about 5.0–25.0%, especially when the wall-forming material is albumin), as may the temperature in the warm chamber (100–250° C., preferably 200–250° C.) and the second step of the process, but The spraying pressure is reduced to less than 2 bar (2×10$^5$ Pa) and is preferably no more than 1.8×10$^5$ Pa, 1.5×10$^5$ Pa or 1.3×10$^5$ Pa. A minimum pressure of 1×10$^5$ Pa is preferred.

The large microspheres of the invention are suitable for use as a deposit echocontrast agent to delineate underperfused areas of microcirculation. We have found that microspheres of mean size 15.0 μm have echogenicities some 4.6×10$^4$ fold higher than similar microspheres of mean size 5.0 μm. Hence, a relatively low dose can be used to image regions deep inside the body which are inaccessible to normal ultrasound techniques. The microspheres can be delivered by known techniques using a catheter to deliver the microspheres to, for example, the capillaries of the liver, kidney or coronary blood vessels. An advantage, compared to classical radiolabelled microsphere studies, is that, following arterial administration, catheter withdrawal and patient stabilisation, multiple plane images may be taken to build a 3D perfusion map of the myocardium or similar capillary bed. Regional myocardial blood flow can be qualitatively assessed in patients with coronary artery disease at the time of angiography by imaging the heart following the direct intracoronary injection of the microspheres. These microspheres are trapped in the microvasculature of the heart during the initial transmit through the coronary circulation. Since only a very small fraction of the capillaries or arterioles is embolized, no detectable adverse haemodynamic or electrophysiological effects are expected. When nutrient blood flow to a segment of the left ventricular myocardium is diminished, as in a region of myocardial scar or in a region supplied by an occluded or severely stenotic coronary artery, the number of microspheres delivered to these segments is reduced. This is appreciated as a focal reduction in activity secondary to regional underperfusion. Because the, microspheres are introduced into the arteries, removal of the microspheres in the capillaries of the lung is avoided.

In the context of angiography, a catheter is placed within the left ventricle via insertion in the femoral artery. X-ray opaque dyes are injected both in the left ventricle and within the coronary arteries themselves. Injection of such agents enables the visualisation of vessels to the 100 $\mu$m diameter level by projecting the 3D information onto a 2D plane. Currently angiography enables stenosis of the major coronary arteries to be identified.

The use of the large microspheres of the invention with ultrasound technology may enable the generation of multiple tomographic images and also 3D reconstruction of images. With the microspheres depositing for sufficient time to enable tomographic images or 3D image reconstruction of the vascular bed, perfusion beds may be delineated. Therefore, as an adjunct to angiography to identify the major causative lesion, a deposit echocontrast agent constituted by the large microspheres of the invention may enable 3D perfusion territories to be identified.

Due to the pressure stability of the preferred microspheres, they retain air and hence echogenicity for a substantial period of time. The microspheres may deposit in the vasculature following catheter administration in a manner similar to classical microsphere studies, reflecting the amount of flow to any given perfusion territory. Imaging of the territory may then be made after catheter withdrawal and patient stabilisation, to enable more optimal images in multiple planes to be gathered. Comparison with a baseline unenhanced image thus enables the perfusion, following a corrective procedure, to be assessed.

The microspheres may be tailored for intracoronary use not only by manipulation of their size and pressure stability but also by their rate of biodegradation.

For intracoronary use, it is preferable to crosslink the large (10–20 $\mu$m) microcapsules at 175° C. for a period of 18–60 minutes, more preferably 20–40 minutes and most preferably 35–40 minutes. This yields microcapsules that are pressure resistant but have a shortened tissue half life compared lo the microcapsules of WO 92/18164 and therefore are more applicable to use in the microcirculation of the myocardium. The tissue half-life can be measured by labelling the microcapsules with $^{125}$I by the Chloramine T method and assessing the organ content of microcapsules by necropsy or the release of $^{125}$I into the urine and faeces.

The "targeted" microspheres of the invention are characterised by having in or on their walls a material to direct or target the microspheres to a desired location in the body.

The "targeted" microspheres of the invention may be prepared by including in or on the wall of the microsphere material which alters the electrical charge of the microsphere.

Thus, a positive or negative charge can be imparted by applying a positively or negatively charged material, respectively, or existing positive or negative charges can be reduced or eliminated. These effects can be achieved in a variety of ways. The final product (ie pressure resistant) microspheres produced by the basic one or two step process described above may be milled as described above and resuspended at a microsphere concentration of $1.0–250\times10^6$/ml in: a 0.5–20.0% w/v solution (preferably 1.0–10.0% w/v, for example about 5%) of a positively or negatively charged material (if polymeric of 1–30 kD, preferably 5–15 kD) and incubated for 5–60 hours (preferably about 8–24 hours) at 5–30° C. (preferably about 20° C.). Positively charged polyamino acids include polylysine, polyaspartamide, polyarginate and polyhistidine. Negatively charged polyamino acids include polyglutamate and polyaspartate. Other negatively charged polymers include phospholipids, hyaluronic acid and polygluconic acid. An advantage of such coated echocontrast agents is to increase the echogenicity of the blood pool to enable signal enhancement of doppler signals.

Alternatively, and more preferably, positive or negative charges on microspheres may be increased by incorporating the material in the spraydrying feedstock in the range of 1–30%, preferably 2–10% w/v. This latter method is particularly preferred for polyglutamate, and for negatively charged additives generally.

Other materials which can be used in the same way to impart a negative charge include anhydrides and chlorides of $C_{1-10}$ organic acids, such as acetic, fumaric and succinic acids. A final concentration of the chloride or anhydride of 5–1000 mg/ml is generally suitable, in a non-polar solvent such as dimethylformamide or tetrahydrofuran. An incubation time of 0.5–5 hours, preferably about R hour, at 5–30° C., preferably about 20° C., is suitable, followed by washing with excess water.

Existing negative charges on the microspheres prepared by the basic spray-drying process may be removed by exposing the microspheres to a carbodiimide agent such as N-ethyl-N$^1$-(3-dimethylaminopropyl)carbodiimide hydrochloride (EDC), at a concentration of about 5–1000 mg/ml for a period of about 5–30 hours (preferably about 16 hours) at 5–30° C. (preferably about 20° C.). Excess reagent is then quenched with, for example, ethanolamine to an equivalent concentration during a further such incubation before the microspheres are washed.

The electrophoretic mobility of the microspheres may be assessed in a Malvern Zeta sizer or in a Pen Kem System 3000 (USA) minielectrophoresis cell, for example for 20 particles in buffers of pH4–10. Preferably, the electrophoretic mobility is in one of the ranges plus or minus $0.001–5.0\times10^{-8}$ m/sec/v/cm. In these ranges the charge upon the microspheres alters their circulatory behaviour. More preferably, the mobility is in one of the ranges plus or minus 0.01 to $0.5\times10^{-8}$ m/sec/v/cm, suitably in one of the ranges plus or minus 0.1 to $0.5\times10^{-8}$ m/sec/v/cm.

In all of these methods of altering the charge on the microspheres, the resulting microspheres may finally be formulated for storage as described above, for example suspending them in a mannitol/Pluronic F68 solution, flash freezing and freeze-drying.

The surface charge of microcapsules can affect the imaging properties of the product through its influence on the in vivo fate of particles. For example, it is known that after intravenous injection negatively charged polystyrene particles are taken up at high efficiency by the liver, whereas particles with a positive charge accumulate initially in the lung. Additionally, it is known that the endothelial cell surface is coated with a glycocalyx carrying a net negative charge at physiological pH values. The inner surface of endothelium may therefore be stained with collodial iron particles carrying a net positive charge. Therefore, in areas of slow or sluggish flow, such as that experienced in the capillary beds of the peripheral vasculature, liver, kidney and myocardium, increasing the net positive charge on the microcapsule shell and endothelial lining may lead to hindered transit through the microcirculation. This creates the possibility of extended imaging windows or even deposit echocontrast agents for analysis of the microvasculature following intravenous administration.

The "long-life" microspheres have an increased circulation time in the body, such that serum $t_{1/2}$ is at least 5 minutes, preferably at least 10 minutes and most preferably at least 15 minutes. Such increased circulation times may be achieved by coating the microspheres with a material which directs the microspheres away from the reticul-endothelial system.

In vivo t½ may be assessed by labelling the microcapsules with $^{125}$I using the well known Chloramine T method, and administering them into the ear vein of a male adult New Zealand rabbit as is generally described in Specific Example 10 below. The serum level of $^{125}$I is measured by gamma counting.

For example, the said material may be one which reduces or substantially prevents "opsonization", the deposition of proteinaceous material (such as fibrinogen) on the microspheres, thus directing the microspheres away from the liver and spleen. Suitable materials with which to coat the microspheres include block copolymers of the poloxamer series (ie polyethylene glycol/polyethylene oxide copolymers), such as poloxamer 338, poloxamer 407 and poloxamer 908.

By prolonging the circulatory half-life of highly pressure resistant air-containing microcapsules, areas of very low flow such as found in the capillary beds are detectable beyond enhanced doppler studies. Abnormal blood flow associated with hepatocellular carcinomas, renal carcinomas, and breast tumours can be detected with use of Doppler techniques. In general, larger malignant turmours show the greatest signal changes, and the abnormal Doppler signals become more difficult to detect in smaller tumours. With malignant breast tumours, for instance, the low signal strength from moving scatterers whose echo is "diluted" by that of stationary solid tissue is one limiting factor in the detection of small tumours. One criterion for the Doppler detection of tumour flow is the inhomogeneity of the spatial distribution of vessels after neovascularization. Contrast enhancement allows the display of smaller vessels and hence increase the utility of this criterion in colour Doppler studies. The agent may enhance backscatter in both tumour and normal vessels. Enhanced blood reflectivity improves detection and differentiation of small tumours in such organs as the breast, liver, kidneys, pancreas and ovaries.

Also, the ultrasound contrast agent may help differentiate areas of normal vascularity from areas of reduced or absent flow due to the presence of tumour or necrosis. The demonstration of normal parenchymal arterial flow within areas that were considered abnormal may help to distinguish normal parenchyma from pseudotumours (focal fatty infiltration of the liver or renal columns of Bertin). Ultrasound contrast agents al so may enhance echoes from arterial blood for the detection of ischemia or occlusion. In cases of partial occlusion, the flow is often fast enough for Doppler detection, but the quantity of blood (which, with tissue attenuation, determines the signal strength) passing through the narrowing may not be great enough to be detected with current Doppler equipment. Under certain circumstances, the introduction of more reflectors can aid delineation of the site of narrowing. A contrast agent may also aid the visualization of collaterals caused by occlusion or severe stenosis.

The long-life microspheres are prepared in the same way as the targeted microspheres described above, in other words the coating material may be applied to a suspension of the spray-dried microspheres before they are freeze-dried or included in the spray feedstock.

A suspension of the microspheres of the invention is generally administered by injection of about 1.0–10.0 ml into a suitable vein such as the cubital vein or other bloodvessel. A microsphere concentration of about $1.0 \times 10^5$ to $1.0 \times 10^{12}$ particles/ml is suitable, preferably about $5.0 \times 10^5$ to $5.0 \times 10^9$.

Although ultrasonic imaging is applicable to various animal and human body organ systems, one of its main applications is in obtaining images of myocardial tissue and perfusion or blood flow patterns.

The techniques use ultrasonic scanning equipment consisting of a scanner and imaging apparatus. The equipment produces visual images of a predetermined area, in this case the heart region of a human body. Typically, the transducer is placed directly on the skin over the area to be imaged. The scanner houses various electronic components including ultrasonic transducers. The transducer produces ultrasonic waves which perform a sector scan of the heart region. The ultrasonic waves are reflected by the various portions of the heart region and are received by the receiving transducer and processed in accordance with pulse-echo methods known in the art. After processing, signals are sent to the imaging apparatus (also well known in the art) for viewing.

In the method of the present invention, after the patient is "prepped" and the scanner is in place, the microsphere suspension is injected, for example through an arm vein. The contrast agent flows through the vein to the right venous side of the heart, through the main pulmonary artery leading to the lungs, across the lungs, through the capillaries, into the pulmonary vein and finally into the left atrium and the left ventricular cavity of the heart.

With the microspheres of this invention, observations and diagnoses can be made with respect to the amount of time required for the blood to pass through the lungs, blood flow patterns, the size of the left atrium ii, the competence of the mitral valve (which separates the left atrium and left ventricle), chamber dimensions in the left ventricular cavity and wall motion abnormalities. Upon ejection of The contrast agent from the left ventricle, the competence of the aortic valve also may be analyzed, as well as the ejection fraction or percentage of volume ejected from the left ventricle. Finally, the contrast patterns in the tissue will indicate which areas, if any, are not being adequately perfused.

In summary, such a pattern of images will help diagnose unusual blood flow characteristics within the heart, valvular competence, chamber sizes and wall motion, and will provide a potential indicator of myocardial perfusion.

The microspheres may permit left heart imaging from intravenous injections. The albumin microspheres, when injected into a peripheral vein, may be capable of transpulmonary passage. This results in echocardiographic opacification of the left ventricle (LV) cavity as well as myocardial tissue.

Besides the scanner briefly described above, there exist other ultrasonic scanners, examples of which are disclosed in U.S. Pat. Nos. 4,134,554 and 4,315,435, the disclosures of which are herein incorporated by reference. Basically, these patents relate to various techniques including dynamic cross-sectional echography (DCE) for producing sequential two-dimensional images of cross-sectional slices of animal or human anatomy by means of ultrasound energy at a frame rate sufficient to enable dynamic visualisation of moving organs. Types of apparatus utilised in DCE are generally called DCE scanners and transmit and receive short, sonic pulses in the form of narrow beams or lines. The reflected signals' strength is a function of time, which is converted to a position using a nominal sound speed, and is displayed on a cathode ray tube or other suitable devices in a manner somewhat analogous to radar or sonar displays. While DCE can be used to produce images of many organ systems including the liver, gall bladder, pancreas and kidney, it is frequently used for visualisation of tissue and major blood vessels of the heart.

The microspheres may be used for imaging a wide variety of areas, even when injected at a peripheral venous site. Those areas include (without limitation): (1) the venous drainage system to the heart; (2) the myocardial tissue and perfusion characteristics during an exercise treadmill test or the like; and (3) myocardial tissue after an oral ingestion or intravenous injection of drugs designed to increase blood flow to the tissue. Additionally the microspheres may be useful in delineating changes in the myocardial tissue perfusion due lo interventions such as (1) coronary artery vein grafting; (2) coronary artery angioplasty (balloon dilation of a narrowed artery); (3) use of thrombolytic agents (such as streptokinase) to dissolve clots in coronary arteries; or (4) perfusion defects or changes due to a recent heart attack.

Furthermore, at the time of a coronary angiogram (or a digital subtraction angiogram) an injection of the microspheres may provide data with respect to tissue perfusion characteristics that would augment and complement the data obtained from the angiogram procedure, which identifies only the anatomy of the blood vessels.

Through the use of the microspheres of the present invention, other non-cardiac organ systems including the liver, spleen and kidney that are presently imaged by ultrasonic techniques may be suitable for enhancement of such currently obtainable images, and/or the generation of new images showing perfusion and flow characteristics that had not previously been susceptible to imaging using prior art ultrasonic imaging techniques.

Figure 2:
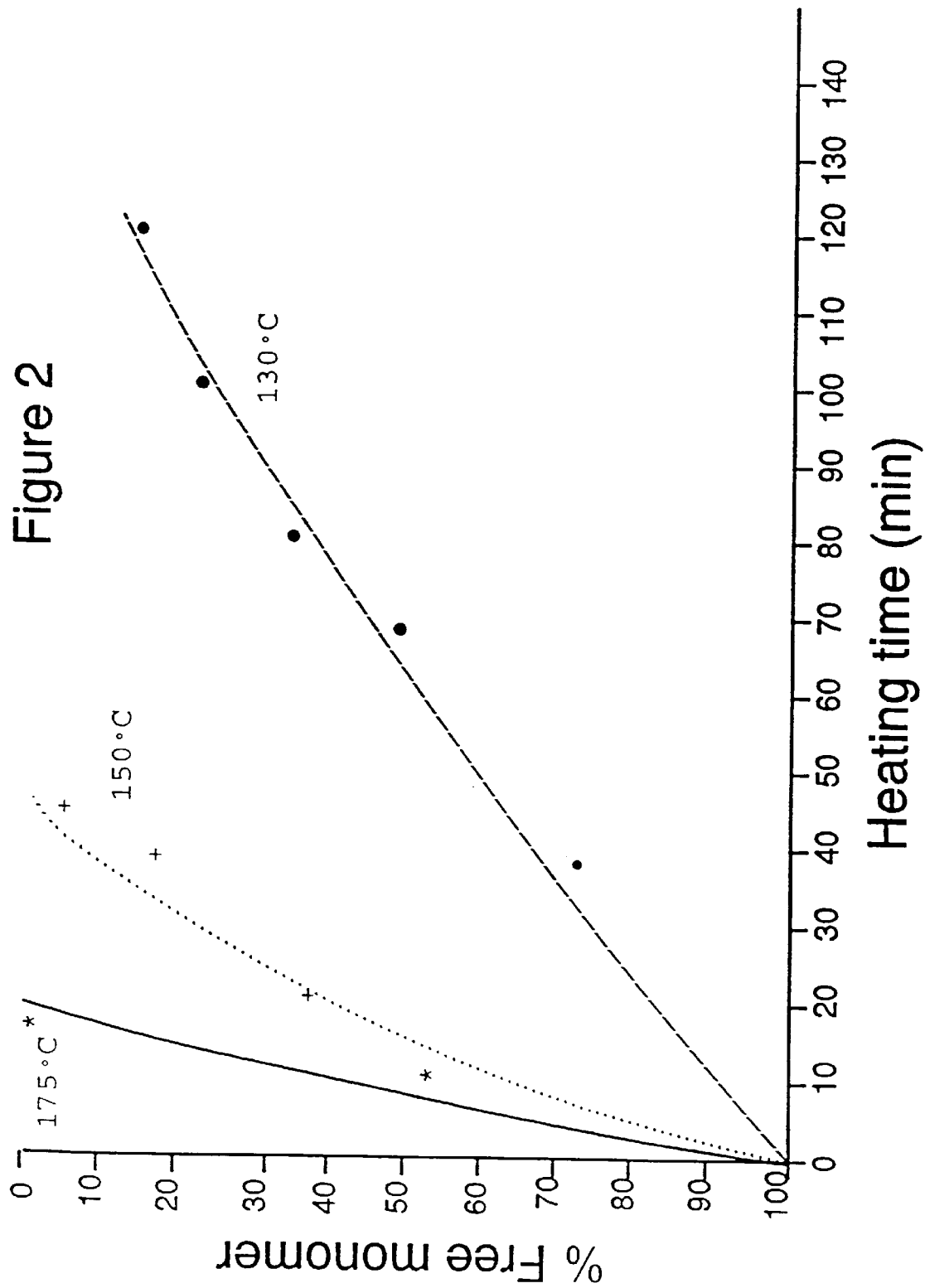
Figure 3:
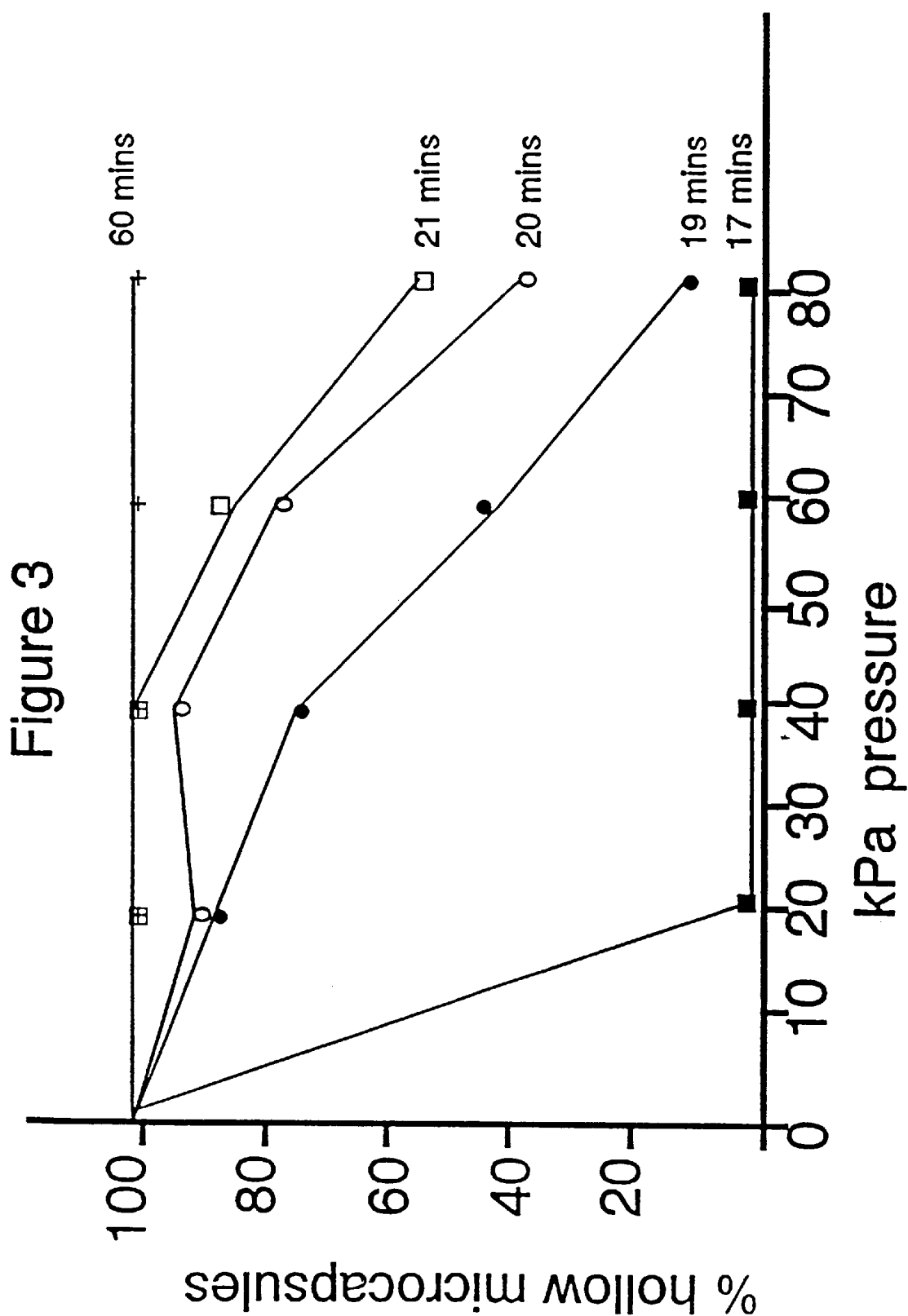
Figure 4:
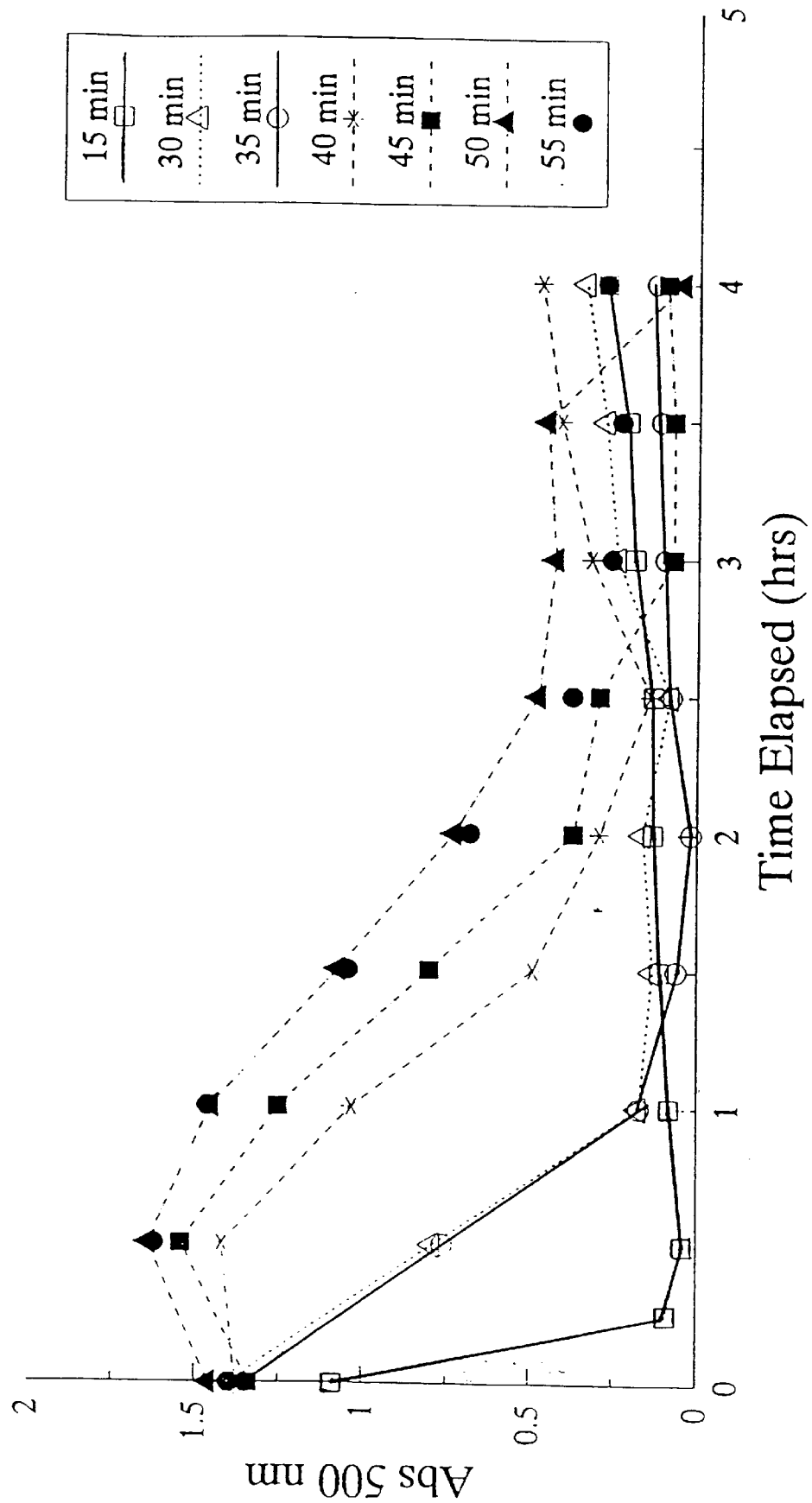
Figure 5A:
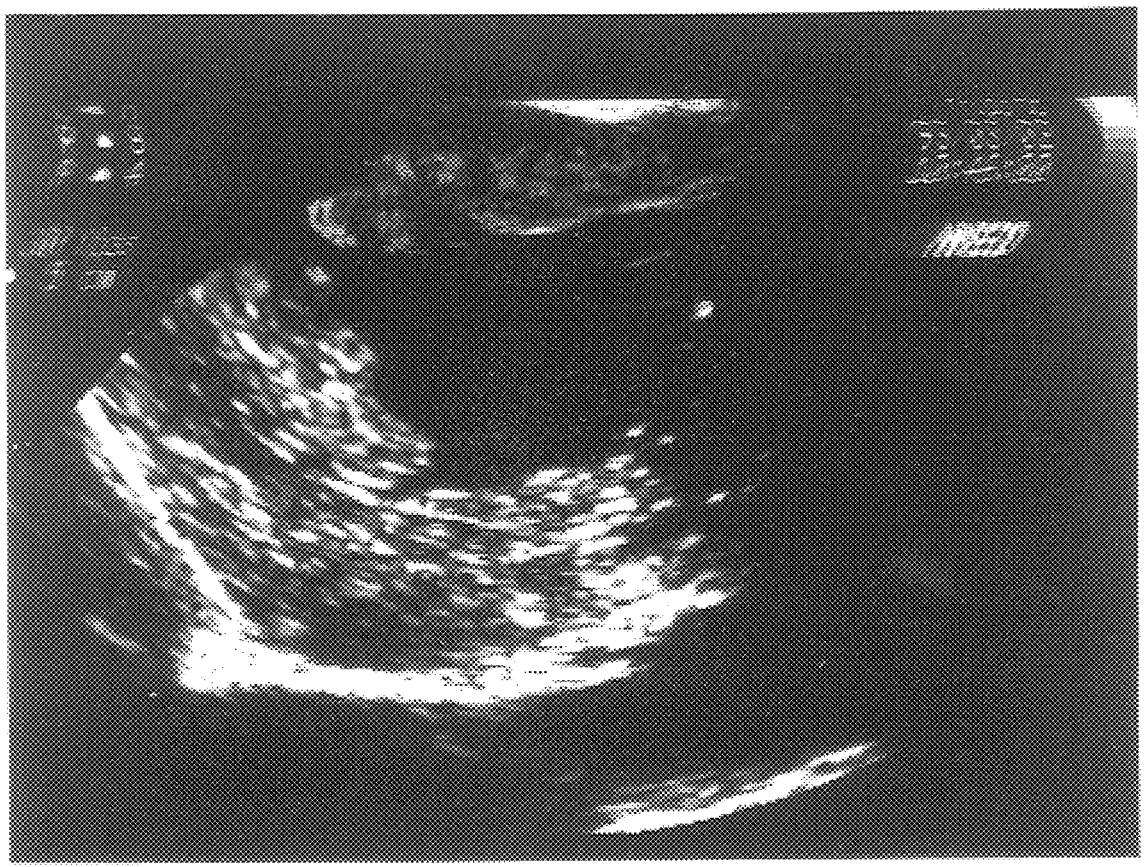
Figure 5B:
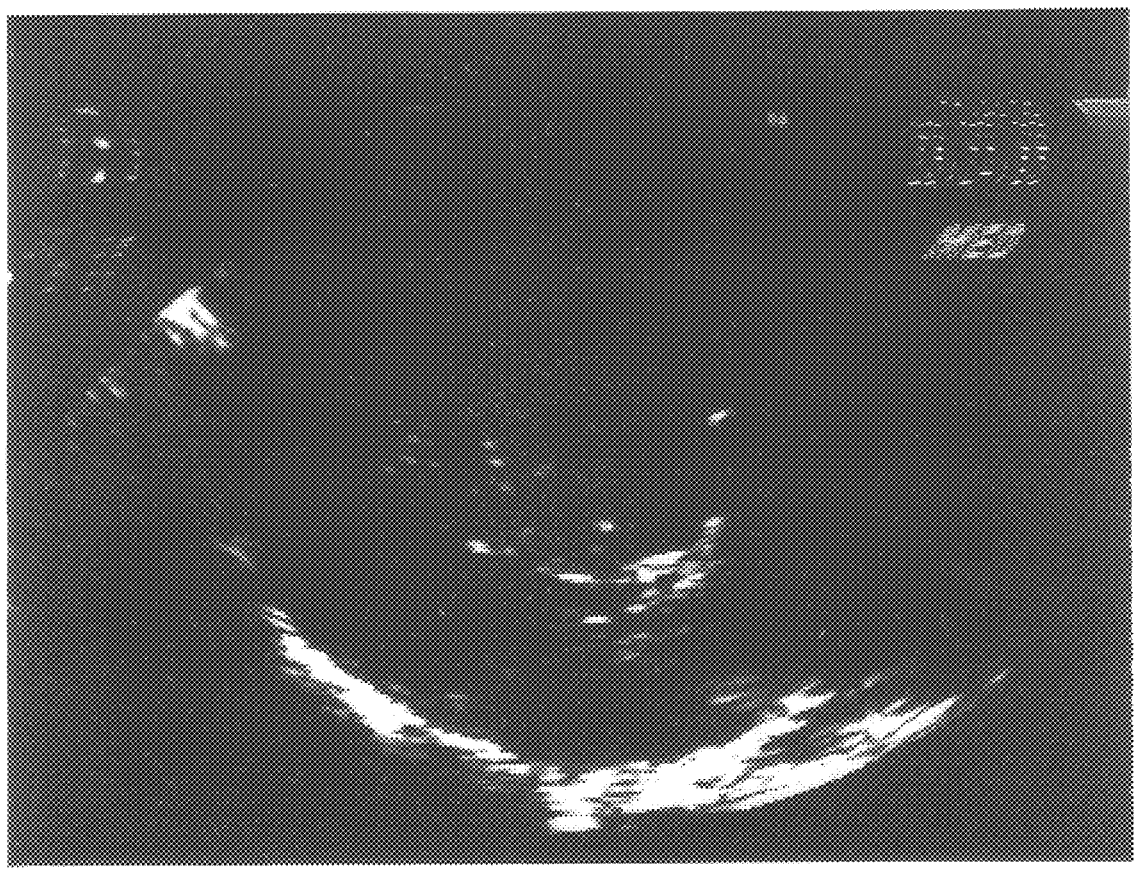

Preferred aspects of the present invention will now be described by way of example and with reference, to:

FIG. 1, which is a partly cut away perspective view from the front and one side of suitable spray-drying apparatus for the first stage of the process of the invention, FIG. 2, which is a graph showing how the degree of fixation of the microsphere walls (in this case albumin) may be controlled by varying the temperature and the heating time in the second step of the process, FIG. 3, which is a graph showing how the pressure resistivity of the microspheres may be varied by altering the length of the heating time in the second step of the process, FIG. 4 is a graph showing how the in vitro biodegradation rate may be varied by varying the length of heating tine in the second step of the process, assessed by a turbidimetric measurement to measure disappearance of microcapsules, and FIGS. 5a and 5b are respective still copies from video tape showing the appearance of pig myocardium before and after injection of 4 million of the large microcapsules of the invention into the left ventricle.

GENERAL PREPARATIVE EXAMPLE 1

A suitable spray dryer (FIG. 1) is available from A/S Niro Atomizer, Soeborg, Denmark under the trade designation "Mobile Minor". Details of its construction are given immediately before the claims herein. It comprises a centrifugal atomizer (Type M-02/B Minor), driven by an air turbine at an air pressure of min 4 bar and up to max 6 bar. At 6 bar an atomizer wheel speed of approx 33,000 rpm is reached. Turning on and off the compressed air to the atomizer is done by means of a valve placed in the instrument panel. The maximum consumption of compressed air to the atomizer is 17 $Nm^3$/h at a pressure of 6 bar. All parts coining into contact with the liquid feed and powder are made of stainless steel AISI 316, except for the pump feed tube and the atomizer wheel, which is made of stainless steel AISI 329, made to resist high centrifugal force. The stainless steel interconnecting pipe system 4 can easily be stripped down for cleaning.

The drying chamber has an inside made of stainless steel AISI 316, well insulated with Rockwool, and covered outside with a mild steel sheeting. The drying chamber is provided with a side light and observation pane for inspection during the operation and steps 5 for access to the chamber top. The roof of the drying chamber is made inside of stainless steel AISI 316 and outside of stainless steel AISI 304. There is a switch 6 for an air valve for activation of the pneumatic lifting device when raising the chamber lid.

An air disperser 2 made of stainless steel AISI 304 is used for distribution of the air in the drying chamber in order to achieve the best possible drying effect. Swirling air is directed around the vaned disc atomiser. An air duct, made of stainless steel AISI 316, provides lateral transportation of the exhaust air and the powder to the cyclone 7, which is made of stainless steel AISI 316 and designed to separate the powder and air.

A closing valve of the butterfly valve type, also made of stainless steel AISI 316 and having a gasket of silicone rubber, is used for powder discharge under the cyclone into a powder collecting glass jar 8 tightly placed under the cyclone by means of a spring device.

A centrifugal exhaust fan 10 made of silumin, complete with 3-phase squirrel-cage motor, 0.25 kW, and V-belt drive with belt-guard, draws air and powder through the drying chamber and cyclone. There is a switch 11 for air flow control via a damper.

An air heater 12 heats the drying air by means of electricity (total consumption 7.5 kWh/h, infinitely variable) and can give inlet air temperatures of up to about 350° C., although this is generally too high for preparing the microspheres of the invention.

The evaporative capacity is as follows:

| | Evaporative capacity | | |
|---|---|---|---|
| Drying Air | Inlet Air Temperature | Outlet Air Temperature | Evaporative Capacity |
| 85 kg/h | 150° C. | 80° C. | 1.3 kg/h |
| 85 kg/h | 170° C. | 85° C. | 1.7 kg/h |
| 80 kg/h | 200° C. | 90° C. | 2.5 kg/h |
| 80 kg/h | 240° C. | 90° C. | 3.4 kg/h |
| 75 kg/h | 350° C. | 90° C. | 7.0 kg/h |

Equipment for two-fluid nozzle atomization may be added, which is made of stainless steel AISI 316, consisting of entrance pipe with nozzle holder and nozzle, to be placed in the ceiling of the drying chamber. The equipment includes an oil/water separator, reduction valve and pressure gauge for compressed air to the two-fluid nozzle. Consumption of compressed air: 8–15 kg/h at a pressure of 0.5–2.0 bar (0.5–2.0×$10^5$ Pa).

A suitable feed pump for transport of wall-forming preparation feed from a reservoir 1 to the atomizer nozzle 3 is a peristaltic pump. The pump is provided with a motor (1×220V, 50 Hz, 0.18 kW) and a continuously variable gear for manual adjustment. A feed pipe made of silicone hose leads from a feed lank (local supply) I through the feed pump to the rotary or nozzle atomization device 3.

An absolute air filter, consisting of prefilter, filter body in stainless steel and absolute air filter, is used for the treatment of the ingoing drying air to render it completely clean. The whole apparatus is controlled via an instrument panel 9.

A 20% solution of sterile, pyrogen-free rHA in pyrogen-free water (suitable for injection) was pumped to the nozzle of a two fluid nozzle atomiser mounted in the commercial spray drying unit described above. The peristaltic pump speed was maintained at a rate of approximately 10 ml/minute such that with an inlet air temperature of 220° C. the outlet air temperature was maintained at 95° C.

Compressed air was supplied to the two fluid atomising nozzle at 2.0–6.0 Bar (2.0–6.0×$10^5$Pa). In this range microspheres with a mean size of 4.25–6.2 µm are obtained.

Typically an increase in mean particle size (by reduced atomisation pressure) led to an increase in the amount of microspheres over 10 µm in size (see Table 1).

TABLE 1

EFFECTS OF ATOMISATION PRESSURE ON FREQUENCY OF MICROSPHERES OVER 10 µM IN DIAMETER

| Atomisation Pressure (×$10^5$ Pa) | % Frequency over 10 µm |
|---|---|
| 6.0 | 0.8 |
| 5.0 | 3.0 |
| 3.5 | 6.6 |
| 2.5 | 8.6 |
| 2.0 | 13.1 |

In the second step of the process, 5 g of microspheres were heated in a glass beaker using a Gallenkamp fan oven. A temperature of 175° C. for 1 hour was sufficient to yield microspheres with 100% fixation as determined by HPLC. The effect of this heat fixation was to increase the in vitro echogenic half life from a few seconds to in excess of 30 minutes. By altering the temperature and length of incubation it is possible to vary the degree of fixation between about 5% and 100%. Examples of heat fixation profiles of varying temperatures are shown in FIG. 2.

Following heat fixation, the microspheres were deagglomerated and dispersed into water in one of two ways. Method 1 involved first mixing the heat fixed spheres with an equal weight of finely milled lactose (mean diameter 5 µm). The mixture was then passed through a Fritscn centrifugal mill with a 0.5 µm screen and 12 tooth rotor. The milled spheres were collected and passed through the mill a second time to ensure complete mixing had occurred. The milled powder was then resuspended in water containing 1 mg.ml$^{-1}$ Pluronic F68. Typically 10 g of microspheres and lactose was added to 100 ml of water and Pluronic F68. Method 2 for deagglomeration involves adding 5 g of the heat-fixed microspheres to 100 ml of water containing 100 mg of Pluronic F68. The microspheres were dispersed using a Silverson homogeniser (model L4R with a 2.54 cm tubular homogenising probe and a high shear screen) and homogenising for 60 seconds.

The resuspended spheres were separated into intact (gas containing) and broken spheres using a flotation technique. The gas-containing spheres were seen to float to the surface over a 1 hour period and were decanted from the sinking fraction which does not contain the gas required.

The separation process can be accelerated by centrifugation. A 30 second centrifugation at 5000×g is sufficient to separate the two fractions.

Following separation the intact microspheres were freeze-dried in the presence of lactose and Pluronic F68. Optimal conditions for freeze drying involved resuspending 30 mg of microspheres in 5 ml of water containing 50 mg of lactose and 5 mg of Pluronic F68. The freeze-dried microspheres can be redispersed in a liquid (eg water, saline) to give a monodisperse distribution.

GENERAL PREPARATIVE EXAMPLE 2

The process of Example 1 was repeated but with the following differences in the first step: a centrifugal atomiser was used instead of a two fluid nozzle; the inlet temperature was 150° C. (with the outlet air temperature still being sustained at 105° C.); and compressed air was supplied to the nozzle at 1.0–6.0×$10^5$ Pa. The wheel rotated at 20–40, 000 rpm and delivered droplets, and subsequently microspheres, with a number mean diameter in the 1.0–8.0 µm range.

GENERAL PREPARATIVE EXAMPLE 3

The second step of the process of Example 1 or 2 was varied as follows. A small aliquot of the microspheres (0.5 g) was heated in a microwave oven such that it received 300–350 watt hours of microwave heat at 2500 mHz. This yielded microspheres in which 90–95% of the monomeric rHA was insoluble (as determined by gel permeation chlomatography) and as a result of this heat fixation their in vitro echogenic half-life increased from a few seconds to in excess of 30 minutes.

GENERAL PREPARATIVE EXAMPLE 4

The second step of the process of Example 1 or 2 was varied as follows. A small aliquot of the microspheres (0.5 g) was sealed under argon in a glass vial. The vial was cooled to 4° C. and then irradiated with a $^{60}$Co gamma radiation source to deliver a 15.0 kGy dose of gamma rays. The irradiation resulted in the formation of microspheres in which 10–15% of the monomeric albumin was insoluble.

GENERAL PREPARATIVE EXAMPLE 5

The second step of the process of Example 1 or 2 was varied as follows. A small aliquot of the microspheres (0.5 g) was sealed under argon in a glass vial. The vial was cooled to 4° C. and then irradiated with a $^{60}$Co gamma radiation source to deliver a 50.0 kGy dose of gamma rays to the microspheres. Following irradiation, the microspheres were incubated in oxygen at 50° C. for 6 hours. The irradiation resulted in the formation of microspheres in which 50–60% of the monomeric rHA was insoluble.

GENERAL PREPARATIVE EXAMPLE 6

The second step of the process of Example 1 or 2 was varied as follows.

A small aliquot of microspheres (0.5 g) was resuspended in 5 ml of ethanol, chloroform or methylene chloride containing a) 1.5% glutaraldehyde, b) 2.0% diphthaloyl chloride or c) 5.0% formaldehyde. The microspheres were stirred for varying times from 10 minutes to 3 hours. The microspheres were removed by filtration and washed thoroughly in the original organic buffer containing 5% ethanolamine, in order to remove excess cross-linking agent. Finally the microspheres were washed in organic solvent and vacuum dried to remove any residual solvents. The extent of insolubilisation may be varied from 5–100% by this method resulting in the extension of in vitro echogenic half-life from 1–2 minutes to in excess of one hour.

GENERAL PREPARATIVE EXAMPLE 7

The two independent steps of microsphere formation and insolubilisation of the shell may be combined in a single process. En this example, the formation of the microspheres and the insolubilisation of the polymeric material are achieved simultaneously during the spray drying process.

A solution of rHA was fed by peristaltic pump to a small reaction chamber, with a separate feed line supplying a 5% solution of a suitable crosslinking agent, eg glutaraldehyde, diphthaloyl chloride or formaldehyde. The residence time in the reaction chamber was such that initial adduct formation between the crosslinking agent and the protein was achieved, but intraprotein crosslinking was prevented. The reaction vessel outlet was fed directly to the two fluid nozzle atomisers mounted in a specially adapted spray drying unit, capable of handling volatile solvents. The conditions of spray drying were as outlined in Example 1. The microspheres were incubated dry at room temperature to allow intraprotein crosslinks to form and then suspended in ethanol containing 5% ethanolamine to quench any remaining crosslinking agent. Thorough washing of the microspheres was performed and finally the microspheres were vacuum dried to remove residual solvent.

GENERAL PREPARATIVE EXAMPLE 8

Assay of Free Monomeric rHA in Microspheres

A 1 ml volume of ethanol was added to 100 mg of microspheres in a 20 ml glass bottle and sonicated for 30 seconds. To this suspension 19 ml of $H_2O$ were added.

The mixture was centrifuged in a bench-top microfuge (Gilson) for 20 seconds and the clear fraction assayed. The assay was performed by loading 50 ml of the fraction automatically onto a Shimadzu LC6A HPLC and chromatographing on a TSK gel permeation column at a flow rate of 1 ml minute$^{-1}$ using sodium phosphate buffer (pH 7.0).

The peak heights representing the rHA monomer were recorded and used lo determine the concentration of monomer using a standard curve between 1 and 10 mgml$^{-1}$ monomeric rHA.

The %-free monomeric rHA was calculated by measuring the monomer concentration in the fixed microspheres and representing this figure as a percentage of the monomer concentration of the unfixed microspheres. The results are given in FIG. 2.

Heating of the spray dried microspheres in an oven (as described in Example 1) results in a decrease in the amount of monomer that can be detected (see FIG. 2). This decrease in detectable monomeric rHA is due to the denaturation and crosslinking of monomeric rHA into insoluble polymers that cannot be assayed by the aforementioned HPLC method.

Using the HPLC method to assess rHA monitor levels, it is clear from FIG. 2 that after 15 minutes incubation there is no free monomeric rHA present in the rHA microspheres. However it is still possible to further crosslink the rHA microspheres by heating for longer periods.

This prolonged heating results in an increased level of microsphere crosslinking which in turn produces microspheres of increasing strength which are correspondingly more resistant to pressure.

By careful control of temperature and time of incubation, it is possible to produce microspheres with a controlled range of crosslinking (and hence pressure resistivity and biodegradation rate).

GENERAL PREPARATIVE EXAMPLE 9

Effects of Incubation Time at 175° C. on the Pressure Resistivity of rHA Microspheres A batch of rHA microspheres from the initial spray-drying step of the process was divided into 5 g aliquots and baked at 175° C. for varying lengths of time as shown in FIG. 3.

Following heat fixation the amount of free monomer was determined as described in Example 8. For each of the incubations shown, there was no monomeric rHA detectable.

The heat-fixed microspheres were disaggregated using a Fritsch centrifugal mill (as described above) and intact, air-containing microspheres recovered by the aforementioned flotation technique. The recovered microspheres were suspended in $H_2O$ containing Pluronic F68 (1 mgml$^{-1}$) at a concentration of $0.5\times10^8$ capsules ml$^{-1}$.

The resuspended, air-containing microspheres were subjected to increased atmospheric pressure by applying pressure with a 50 ml syringe whilst containing this suspension in a closed container (25 ml polystyrene container).

For each of the pressures assessed, the individual microsphere suspension was pressurised to the selected pressure and maintained at this pressure for 5 seconds before releasing the pressure. For each suspension analysed the pressure increase was performed 3 times. The pressure in the closed container was assessed by an RS hand-held manometer.

Following pressurisation the microsphere suspensions were assessed by light microscopy and image analysis and the % air-containing to non-air-containing microspheres assessed. This analysis is performed since only the air-containing microspheres are functional in enhancing ultrasound echocontrast.

As can be seen in FIG. 3, microspheres that are fixed for 60 minutes at 175° C., as described in Example 1, are stable at all of the pressures to which they were subjected in this experiment.

By careful control of the length of incubation at this particular temperature (175° C.) it is possible to produce batches of microspheres with different degrees of crosslinking which in turn are resistant to varying degrees of pressure increase.

Using this careful control of crosslinking by adjusting the length and temperature of incubation it is possible to produce batches of air-containing microspheres that are specifically designed to withstand a designated pressure increase.

The temperature used to crosslink the microspheres can vary infinitely, as can the length of incubation time.

GENERAL PREPARATIVE EXAMPLE 10

Microsphere Classification

An advantage of the process of the invention is that it enables the median size and size distribution of the microspheres to be controlled. However, one can further select desired sizes if one wishes, for example by flotation. In a homogeneous dispersion of microspheres, larger particles will rise to the surface faster than smaller particles due to the lower density (more encapsulated air) of the larger particles. Hence, by allowing the dispersion to stand, the particle size distribution will change at any level of the solution with respect to time.

Microspheres were dispersed in 2000 ml of aqueous solution containing 6% w/v sodium chloride and 0.1% w/v Pluronic F68 in a glass bottle giving a liquid column of approximately 165 mm. A sampling tube was placed 50 mm below the upper liquid surface to enable removal of samples at timed intervals.

By altering the standing time and sodium chloride concentration, it was possible to produce a variety of particle size distributions and classify microspheres down to 2 μm.

Other wet techniques for classification include hydrodynamic chromatography and field flow fractionation. 'Dry' techniques using the principles of elutriation and cross flow separation are commercially available in the form of the Microsplit (British Rem.), Zig-zag (Alpine) and Turbo (Nissuin) classifiers. The elbow jet classifier produced by Nitettsu Mining Co uses a different principle (the Coanda Effect) which could also achieve good results for the classification of microspheres.

SPECIFIC EXAMPLE 1

A solution of human albumin (5% w/v) is spray-dried at an inlet temperature of 220° C. and an air pressure of 1.5 bar as in General Preparation Example 1. The resulting particles are heat fixed for a period of 20 minutes at 175° C. in an air oven. The samples are deagglomerated by milling with mannitol and the particles are resuspended in a solution of 10 mg/ml mannitol and 0.06 mg/ml pluronic F68. The intact particles are creamed off and the microsphere suspension is freeze-dried.

Particles predominantly of 10–20 μm are produced which contain air and are substantially pressure resistant.

SPECIFIC EXAMPLE 2

Polylysine at a concentration of 5% w/v was resuspended with the microspheres of General Preparative Example 2 ($100\times10^6$ particles/ml) and incubated overnight at 20° C. Mannitol and Pluronic F68 were added at the concentration described in Specific Example 1 and the suspension was subsequently flash frozen and freeze dried.

SPECIFIC EXAMPLE 3

Hyaluronic acid at a concentration of 5% w/v was incubated overnight with resuspended microspheres prepared as in General Preparative Example 1 at 20° C. (100×106 microspheres/ml). Mannitol and Pluronic F68 were added to a concentration of 10 and 0.06 mg/ml respectively and the suspension then flash frozen and freeze dried.

SPECIFIC EXAMPLE 4

Microspheres according to General Preparative Example 3 were resuspended in a solution of DMF (Dimethylformamide) at a concentration of $100\times10^6$ particles/ml. Acetic anhydride was added to give a final acid anhydride concentration of 100 mg/ml. The microsphere mixture was incubated at 20° C. for 1 hour then diluted with water and filtered and washed with excess water over a 1 hour period. The microspheres were formulated in Mannitol and Pluronic F68 as described above. This method imparts negative charges.

SPECIFIC EXAMPLE 5

Microspheres according to General Preparative Example I were resuspended in an aqueous solution at a concentration of $100\times10^6$ particles/ml. An aqueous solution of carbodiimide was added to the microsphere suspension to give a final concentration of 100 mg/ml. After incubation at 16 hours at 20° C., excess reagent was quenched by the addition of glycine to an equivalent concentration and further incubation for 16 hours at 20° C. The microspheres were washed with water then formulated as described above. This procedure eliminates negative charges.

SPECIFIC EXAMPLE 6

Microcapsules of general preparative method 2 were formulated with polaxamer 407 and mannitol at a concentration of 0.1 and 10 mg/ml respectively. The suspension was flash frozen and freeze dried as described in the earlier examples.

SPECIFIC EXAMPLE 7

Poly-L-lysine (15–25 kDa) was added to the rHA feedstock (20% w/v) to a final concentration of 0.5% w/v prior to spray drying. The method of general example 2 was followed to yield microcapsules with increased positive charge upon the shell.

SPECIFIC EXAMPLE 8

Poly-L-glutamate (15–30 kDa) was added to the rHA feddstock (20% w/v) to a final concentration of 0.5% w/v prior to spray drying. The method of general preparative example 2 was followed to yield microcapsules with increased negative charge upon the shell.

SPECIFIC EXAMPLE 9

Microspheres of Specific Example 1 may be used in an in vivo analysis to establish the feasibility of delineating perfusion territories in the myocardium of a pig heart.

A 25 kg Yorkshire swine is anaesthetised and fully ventilated according to the methodology outlined in Ten Cate et al (1992) *Cardiovascular Research 26, 32–39.* A 5 French catheter is inserted via the femoral artery, ascending aorta and aortic root into the left ventricle. Injection of 4 million microcapsules of Specific Example 1 is made and 2 dimensional transthoracic echocardiography in the short axis plan using a Hewlett Packard sono's 1000, equipped with a 3.5 MHz transducer, is used to assess regional perfusion. Intense opacification of the myocardium was observed (see FIG. 5), showing that no redistribution of hollow microcapsules occurred over the 2 hour period. Subsequent injections of microcapsules into the left ventricle resulted in sequential dose-dependent brightening of the myocardium. Haemodynamic parameters were monitored and showed no adverse effect of injection of these low levels of microcapsules.

SPECIFIC EXAMPLE 10

Microcapsules of Specific Example 6 were injected into the ear vein of a mildly sedated New Zealand rabbit (4.5 kg) at a concentration of 300 million particles/ml. Femoral artery Doppler signals were assessed using an Interspect 7000 model equipped with a 10 MHz transducer. Baseline signals prior to contrast injection were obtained to enable comparison of Doppler signals before and after contrast injection. Once baseline signals were obtained, the instrument's time intensity gain controls were not altered.

Following contrast injection, visible prolonged Doppler enhancement of the myocardium was obtained, lasting for several beats or several minutes depending upon the dose size of contrast agent administered.

The T½ was determined by videodensitometry of the spectral Doppler signals as follows. The gain settings were adjusted to give barely visible signals before contrast injection. As the contrast entered the femoral artery the signal increased, peaked and then decayed. Videodensitometry was performed on the individual peaks of flow and a time intensity curve plotted. The T½ was calculated as the time taken for the contrast effect to diminish to half its peak value. Videodensitometry of spectral Doppler signals revealed a reproducible contrast effect following intravenous injection of the microcapsules which was significantly prolonged over the signals produced by microcapsules formulated according to PCT/GB92/00643.

We claim:

1. A method comprising the steps of:
   (i) providing a pharmaceutically acceptable composition of hollow microcapsules having a mean diameter of between 12.0 and 25.0 $\mu$m, and
   (ii) introducing said composition via a catheter into a human or animal body such that said microcapsules deposit in the vasculature of said human or animal.

2. The method of claim 1, further comprising delineating under-perfused areas of microcirculation with said deposited microcapsules.

3. The method of claim 2 wherein said catheter is introduced into a coronary artery or the left ventricle of the heart of said human or animal.

4. The method of claim 1 wherein said method additionally comprises:
   (iii) subjecting said human or animal body to ultrasound, and
   (iv) forming an image resulting from the reflection of the ultrasound by said deposited microcapsules.

* * * * *

UNITED STATES PATENT AND TRADEMARK OFFICE
CERTIFICATE OF CORRECTION

PATENT NO. : 5,957,848
DATED : September 28, 1999
INVENTOR(S) : Sutton et al.

It is certified that error appears in the above-identified patent and that said Letters Patent is hereby corrected as shown below:

At column 1, at line 8, please delete "PCT/GB93/0209" and insert therein

--PCT/GB93/02091--.

Signed and Sealed this

Sixteenth Day of January, 2001

Attest:

Q. TODD DICKINSON

*Attesting Officer*  *Commissioner of Patents and Trademarks*

UNITED STATES PATENT AND TRADEMARK OFFICE
CERTIFICATE OF CORRECTION

PATENT NO.    : 5,957,848
DATED         : September 28, 1999
INVENTOR(S)   : Sutton *et al.*

It is certified that error appears in the above-identified patent and that said Letters Patent is hereby corrected as shown below:

Title page, item [73],
Line 1, ("Assignee"), please delete "Andaris Limited" and insert therein -- Quadrant Healthcare (UK) Limited --.

Column 1,
Line 8, please delete "PCT/GB93/0209" and insert therein -- PCT/GB93/02091 --.

Signed and Sealed this

Second Day of October, 2001

*Attest:*

NICHOLAS P. GODICI
*Attesting Officer*    *Acting Director of the United States Patent and Trademark Office*